(12) United States Patent
Han et al.

(10) Patent No.: US 8,973,603 B2
(45) Date of Patent: Mar. 10, 2015

(54) GAS FLOW REGULATING DEVICE

(75) Inventors: Steve Han, Upland, CA (US); Alex Stenzler, Long Beach, CA (US)

(73) Assignee: CareFusion 2200, Inc., San Diego, CA (US)

( * ) Notice: Subject to any disclaimer, the term of this patent is extended or adjusted under 35 U.S.C. 154(b) by 706 days.

(21) Appl. No.: 12/372,087

(22) Filed: Feb. 17, 2009

(65) Prior Publication Data

US 2010/0206309 A1 Aug. 19, 2010

(51) Int. Cl.
*F16K 31/12* (2006.01)
*G05D 7/01* (2006.01)
*A61B 5/097* (2006.01)

(52) U.S. Cl.
CPC .............. *G05D 7/0106* (2013.01); *A61B 5/097* (2013.01)
USPC ...................................... 137/505.25; 137/510

(58) Field of Classification Search
USPC ................. 137/505.25, 505.13, 510
See application file for complete search history.

(56) References Cited

U.S. PATENT DOCUMENTS

| | | | |
|---|---|---|---|
| 2,184,773 A | 12/1939 | Browning | |
| 2,519,349 A | 8/1950 | Burns et al. | |
| 2,553,919 A * | 5/1951 | Hug et al. | 137/495 |
| 3,070,108 A | 12/1962 | Fischer | |
| 3,480,033 A | 11/1969 | Holloway | |
| 3,563,508 A * | 2/1971 | DeLorenzo | 251/63.5 |
| 3,688,794 A | 9/1972 | Bird et al. | |
| 3,995,656 A | 12/1976 | Mills, Jr. | |
| 4,207,884 A | 6/1980 | Isaacson | |
| 4,241,757 A | 12/1980 | Bron | |
| 4,416,270 A * | 11/1983 | Havstad | 601/105 |
| 4,428,397 A | 1/1984 | Bron | |
| 4,572,477 A | 2/1986 | Phlipot et al. | |
| 4,579,826 A | 4/1986 | Bolton et al. | |
| 4,879,998 A | 11/1989 | Moellers | |
| 4,922,955 A * | 5/1990 | Uri | 137/505.25 |
| 5,065,746 A | 11/1991 | Steen | |
| 5,127,400 A | 7/1992 | DeVries et al. | |
| 5,135,023 A * | 8/1992 | Ross | 137/505.11 |

(Continued)

FOREIGN PATENT DOCUMENTS

EP 1 054 312 A2 11/2000
JP H02-071299 U 5/1990

(Continued)

OTHER PUBLICATIONS

PCT Search Report (mailed Jun. 7, 2010); 15 pgs.

(Continued)

*Primary Examiner* — Craig Schneider
*Assistant Examiner* — Ian Paquette
(74) *Attorney, Agent, or Firm* — McDermott Will & Emery LLP (57) ABSTRACT

A gas flow regulating device including a housing assembly, an inlet tube assembly, and a biasing device. The housing assembly has a main housing, a valve seat body, and a distal plate forming an outlet orifice. The inlet tube assembly includes a proximal inlet end, a tube forming a lumen, and a flange, and is slidably disposed within the main housing, biased to an open state by the biasing device. The flange separates middle and constant pressure chambers within the housing assembly. The inlet tube assembly is transitionable to a closed state in response to pressure in the constant pressure chamber to generate a relatively constant flow rate of air exiting the device via the outlet orifice.

18 Claims, 6 Drawing Sheets

(56) References Cited

U.S. PATENT DOCUMENTS

| | | | |
|---|---|---|---|
| 5,307,834 A * | 5/1994 | Tatarek-Gintowt et al. | 137/505.11 |
| 5,363,876 A | 11/1994 | Nash | |
| 5,385,141 A | 1/1995 | Granatiero | |
| 5,415,767 A * | 5/1995 | Schuler et al. | 210/191 |
| 6,102,038 A | 8/2000 | DeVries | |
| 6,158,457 A | 12/2000 | Byrd et al. | |
| 6,761,185 B1 | 7/2004 | De Leeuw | |
| 6,983,761 B2 * | 1/2006 | Henley et al. | 137/505.25 |
| 7,048,001 B2 * | 5/2006 | Youngberg et al. | 137/505.25 |
| 7,181,953 B1 * | 2/2007 | Street | 73/29.05 |
| 2004/0003848 A1 * | 1/2004 | Callies | 137/505.25 |
| 2006/0278277 A1 * | 12/2006 | Carter | 137/505.25 |
| 2008/0178883 A1 | 7/2008 | Gorski | |
| 2009/0242043 A1 * | 10/2009 | Lev et al. | 137/505.25 |

FOREIGN PATENT DOCUMENTS

| | | |
|---|---|---|
| JP | 2003-502772 | 1/2003 |
| RU | 02122195 | 11/1998 |
| RU | 00076568 | 9/2008 |
| WO | WO 00/79357 | 12/2000 |
| WO | WO 2008/156986 | 12/2008 |

OTHER PUBLICATIONS

English Translation of Japanese Office Action dated Sep. 17, 2003.
Russian Office Action mailed in Russian Patent Application No. 2011138268 on Dec. 21, 2013; 3 pages.

* cited by examiner

GAS FLOW REGULATING DEVICE

BACKGROUND

The present disclosure relates generally to a gas flow regulating device. More particularly, it relates to devices for regulating the flow of gaseous samples from a patient's respiratory system and suitable for various applications requiring a constant flow of air or other gaseous substance, independent of the originating volume and pressure.

The air exhaled from a patient is important for diagnosing many diseases through analysis of certain substance concentrations in the exhaled air. For example, it is often desirable to analyze the air exhaled from a patient to determine whether the breath contains a particular compound, such an ethyl alcohol or carbon dioxide, or a non-chemical such as a particular microorganism. However, since the pressure of the exhaled air varies from patient to patient, and also during the exhalation process, the volume of air passing through a testing unit during a given unit of time will vary considerably, leading to inconsistent and/or unreliable results. Therefore, there is a need for a device that will create a constant flow of exhaled air to a testing mechanism, independent of the pressure of the exhaled air.

In light of the above, a need exists for improved gas flow regulating devices used for patient air sampling.

SUMMARY

One aspect provides a gas flow regulating device for use as part of in a medical system for sampling a patient's breath, including a housing assembly, an inlet tube assembly, and a biasing device. The housing assembly has a main housing, a valve seat body, and a distal plate, and forms a middle chamber and a constant pressure chamber. The inlet tube assembly defines a proximal inlet end, and includes an inlet tube forming a lumen, and a flange. The inlet tube assembly is slidably disposed within the middle chamber, with the biasing device biasing the inlet tube assembly to an open state in which the lumen is open to the constant pressure chamber. With this construction, relatively constant flow from the constant pressure chamber via an outlet orifice in the distal plate is provided by the inlet tube assembly slidably transitioning to a closed state in which the lumen is sealed from the constant pressure chamber in response to an increase in pressure in the constant pressure chamber to generate a force greater than a biasing constant of the biasing device, and returning to the first state in response to a decrease in pressure in the constant pressure chamber.

DETAILED DESCRIPTION

Figure 1:
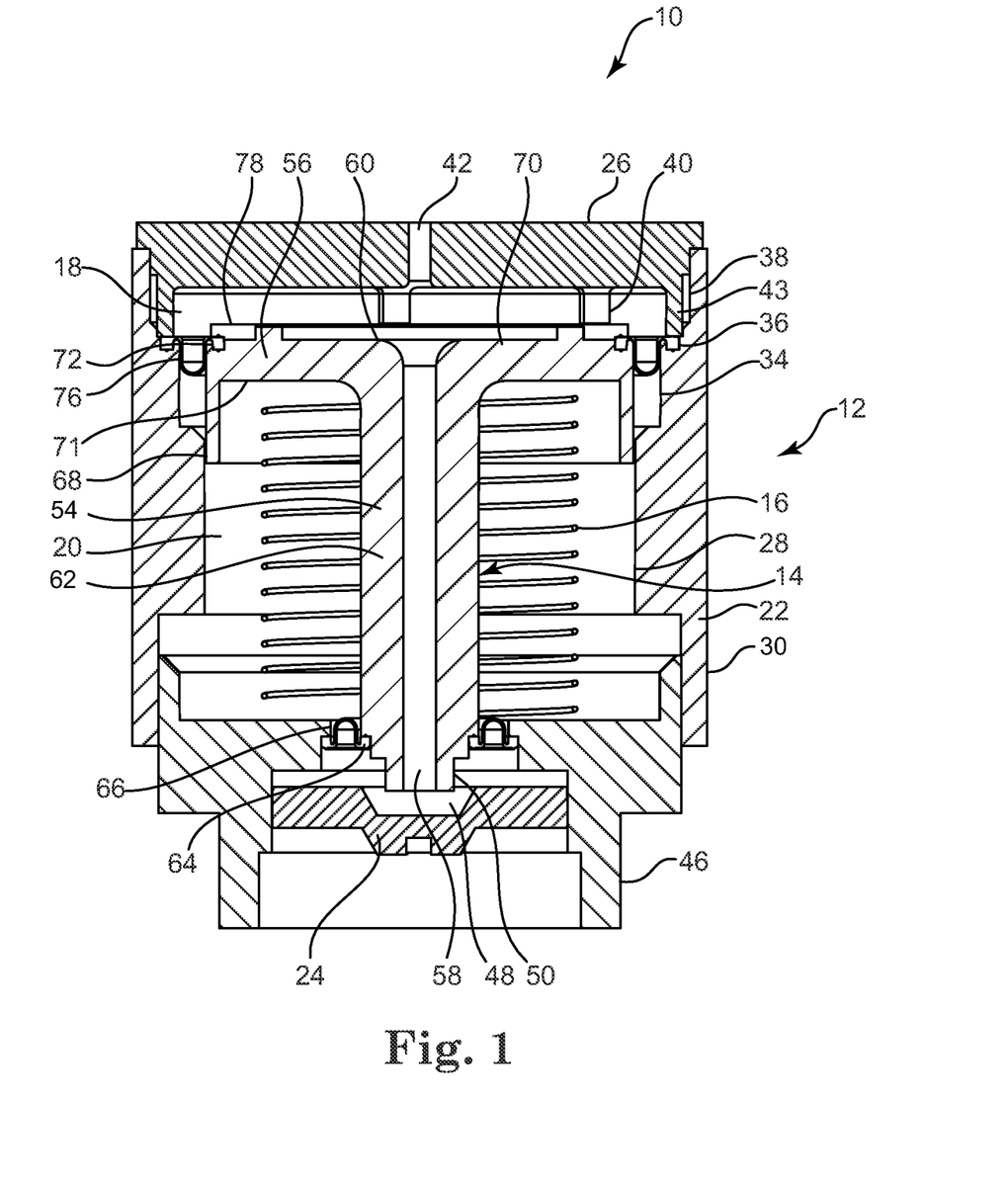
FIG. 1 is a sectional view of a flow regulating device in accordance with principles of the present disclosure.

Some aspects in accordance with the present disclosure relate to a gas flow regulating device for use in regulating flow of air from a patient as part of a medical system. One embodiment of a flow regulating device 10 in accordance with the present disclosure is shown in FIG. 1 and includes a housing assembly 12, an inlet tube assembly 14, and a biasing mechanism 16. Details on the various components are provided below. In general terms, however, the inlet tube assembly 14 and biasing mechanism 16 are disposed within the housing assembly 12. Additionally, two chambers are formed within the housing assembly 12, a constant pressure chamber 18 and a middle chamber 20. The biasing mechanism 16 biases the inlet tube assembly 14 to an open state as shown, with the inlet tube assembly 16 being selectively slidable within the middle chamber 20 to a closed state (not shown) in response to pressures within the constant pressure chamber 18.

Figure 2:
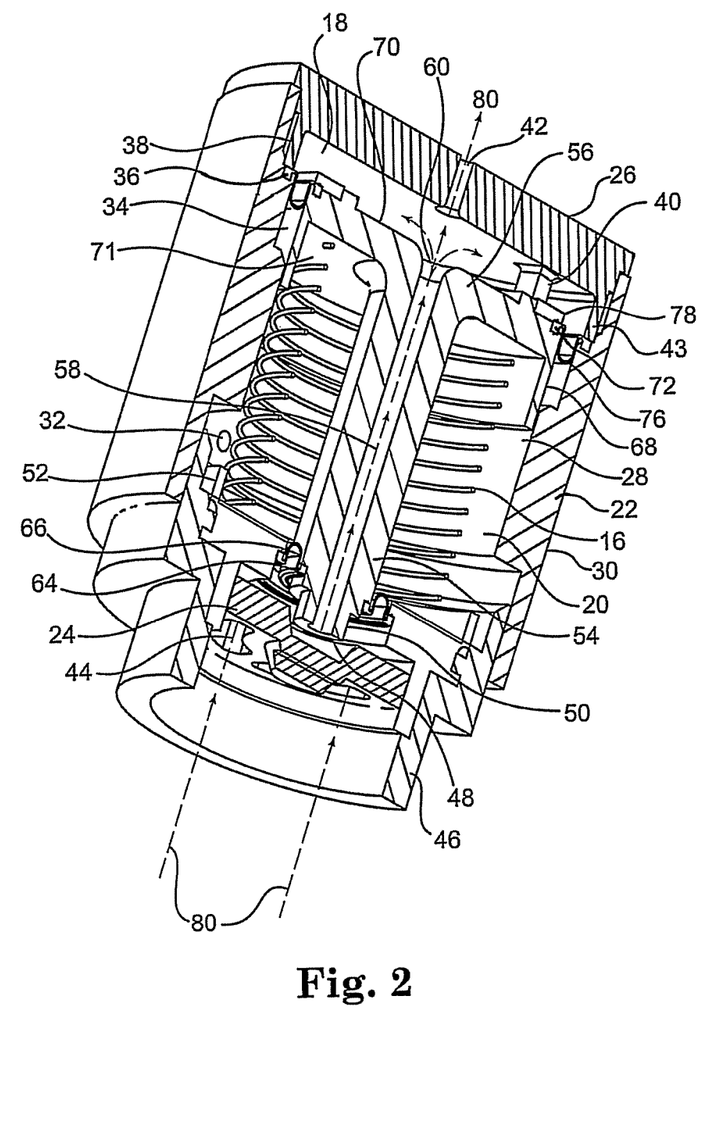
FIG. 2 is a perspective, sectional view of the flow regulating device of FIG. 1.
Figure 3:
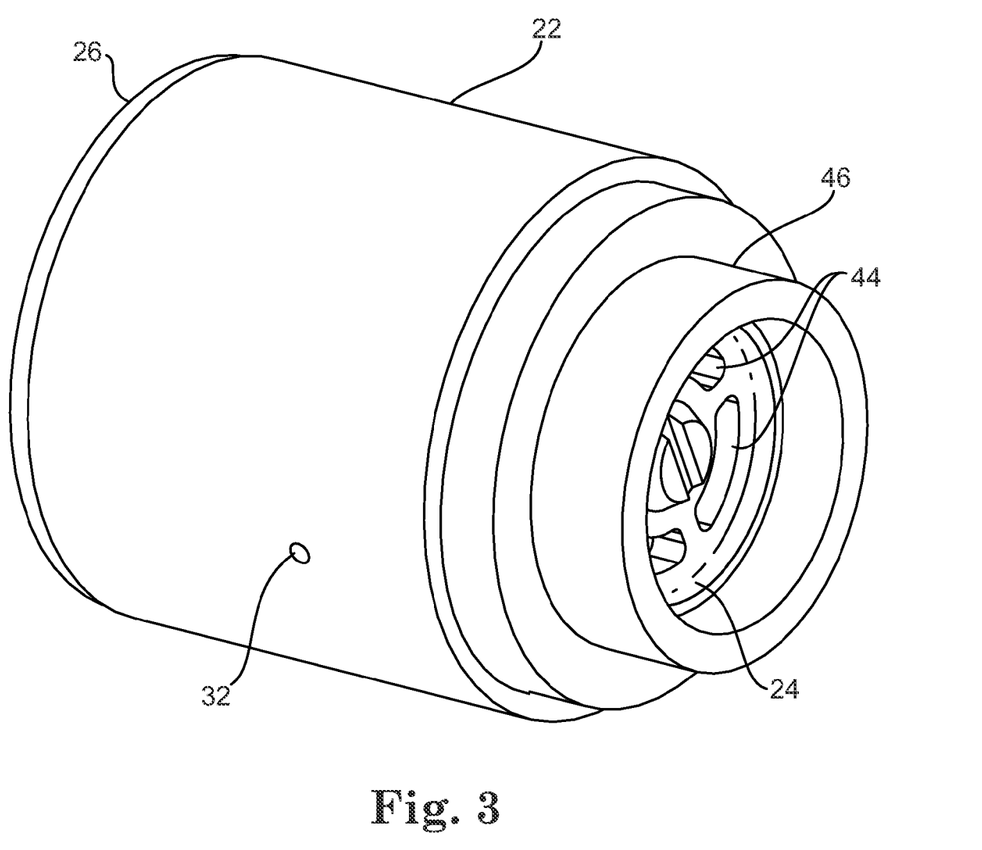
FIG. 3 is a side perspective view of the flow regulating device of FIG. 1.
Figure 4:
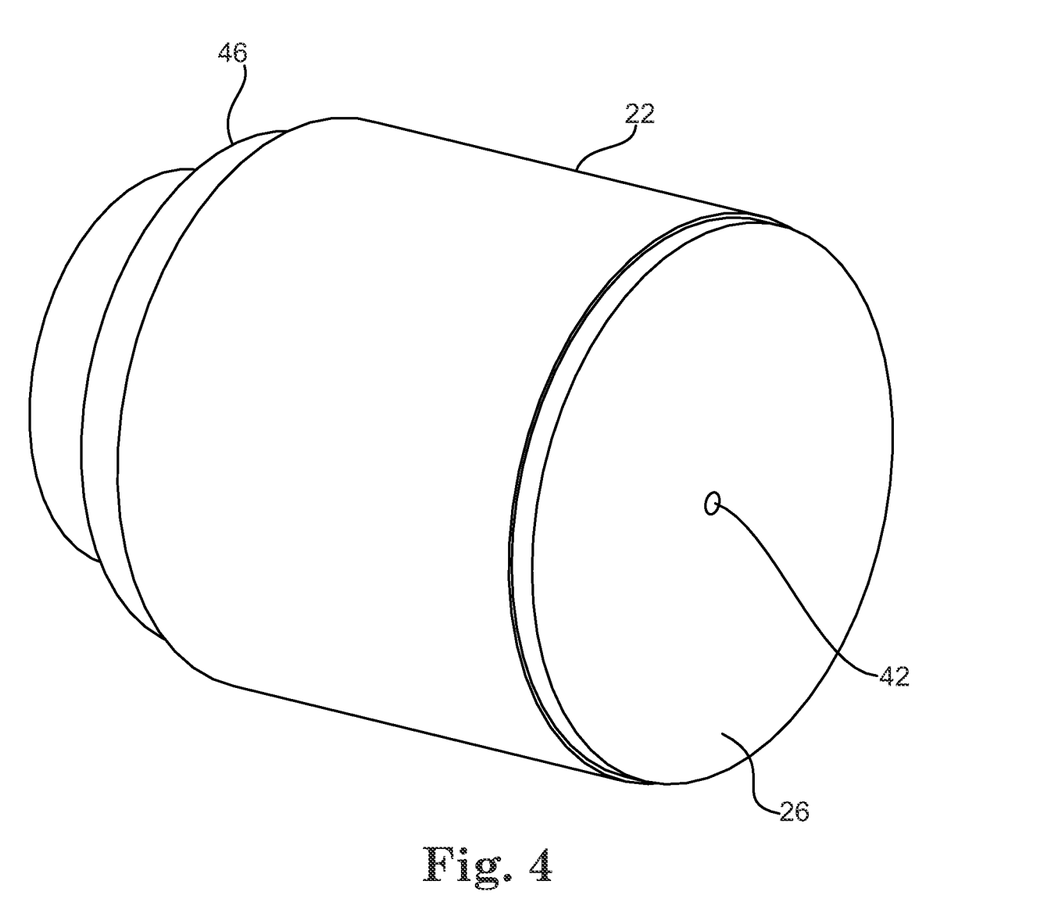
FIG. 4 is an end perspective view of the flow regulating device of FIG. 1.

With the above in mind, the housing assembly 12 includes a main housing 22, a valve seat body 24, and a distal plate 26. As illustrated in FIG. 1, the main housing 22 may be generally cylindrical, forming an interior surface 28 and an exterior surface 30. As illustrated in FIGS. 2 and 3, the main housing 22 includes a flow port 46 which is configured to connect directly to a patient's mouth, an artificial airway of a patient, or other medial device. The flow port 46 may be formed integrally with the main housing 22, or assembled later. The main housing 22 may also include an interior guide 52 extending for a distance from proximal to the valve seat body 24 towards the distal plate 26. The main housing 22 forms at least one bleed hole 32 extending from the interior surface 28 to the exterior surface 30, and thereby open to ambient. The main housing 22 may be formed of any plastic, metal or hardened rubber or other suitable material.

With further reference to FIGS. 1 and 2, the interior surface 28 of the main housing 22 optionally forms a channel 34, a groove 36, and/or a circumferential recess 38. The channel 34 and the groove 36 can extend about a perimeter of the interior surface 28, with the groove 36 being formed radially outside of the channel 34. The circumferential recess 38 also may extend about the perimeter of the interior surface 28, and is configured to couple with the distal plate 26. The distal plate 26 is described in greater detail below, and is generally configured for removable assembly to the main housing 22 at the circumferential recess 38. The distal plate 26 may be threaded (not shown) or otherwise configured (e.g. snap-fit) at the circumferential recess 38 in order to form a sealed connection with the main housing 22. In yet other constructions, the distal plate 26 is more permanently affixed to and/or formed integral with the main housing 22. Further, additional components useful in establishing and maintaining the desired sealed connection, such as a coupling, a seal, an o-ring, etc. may be included with the housing assembly 12.

The valve seat body 24 and the distal plate 26 are positioned at opposing ends of the main housing 22. With additional reference to FIG. 3, the valve seat body 24 further forms through holes 44 for incoming airflow. The valve seat body 24 forms a seat 48 sized to receive and fluidly seal an end of the inlet tube assembly 14, as described below. Thus, the valve seat body 24, and in particular the seat 48, is formed of a material capable of forming a fluid seal, such as rubber or similar materials.

Returning to FIGS. 1 and 2, the distal plate 26 may have at least one extension 40, which when assembled with the main housing 22, protrudes into the main housing 22. The distal plate 26 also forms an outlet orifice 42. As described below, air within the constant pressure chamber 18 is released from the device 10 via the outlet orifice 42; thus, a diameter of the outlet orifice 42 dictates a flow rate of the outgoing air. Stated otherwise, a desired flow rate of air released from the device 10 can be achieved by employing a distal plate having an appropriate, correspondingly-sized outlet orifice 42. In some embodiments, then, the device 10 of the present disclosure includes two or more distal plates 26 each with a different diameter outlet orifice 42. The desired distal plate 26 is then selected by the user and assembled to the main housing 22, with a diameter of the corresponding outlet orifice 42 appropriately sized to generate the desired outlet pressure/flow rate. Alternatively or in addition, the distal plate 26 can optionally include one or more adjustment components (not shown) associated with the outlet orifice 42 that allow a user to alter or select an effective diameter of the outlet orifice 42. The distal plate 26 may include one or more additional features, such as hub 43, extending proximal to the outer perimeter of the distal plate 26 for a distance in generally the same direction as the at least one extension 40.

The housing assembly 12 is sized to receive the inlet tube assembly 14. The inlet tube assembly 14 defines a proximal end 50, and includes a tube 54 and a flange 56. As illustrated in FIGS. 1 and 2, the tube 54 is cylindrically shaped and forms a lumen 58 that is open at the proximal end 50 and a distal end 60 of the inlet tube assembly 14. In one embodiment, the lumen 58 has a uniform diameter. The proximal end 50 of the inlet tube assembly 14 is oriented to correspond with, and selectively fluidly seal against, the seat 48 of the valve seat body 24. The tube 54 has a proximal region 62 terminating at the proximal end 50. In one embodiment, the proximal region 62 forms a ridge 64 for assembly to a flexible membrane body as described below.

At the distal end 60 of the inlet tube assembly 14, the flange 56 has a radial wall 68, a distal face 70, a proximal face 71, and an outer groove 72 formed on the distal face 70. The radial wall extends proximally from the proximal face 72, and is radially spaced from the tube 54 to provide a surface for slidably engaging the interior surface 28 of the main housing 22. The distal face 70 may be smooth or include variations in the surface.

The inlet tube assembly 14 is preferably made of the same material (a rigid or semi-rigid material such as plastic, metal or hard rubber, for example) and integrated as a single piece.

Also configured to fit within the housing assembly 12 is the biasing mechanism 16. The biasing mechanism 16 may be a helical spring or other device which exerts a force. The biasing mechanism 16 is pretensioned to a force (e.g., a spring constant k) corresponding to a desired pressure in the constant pressure chamber 18 and will not compress until the pressure in the constant pressure chamber 18 generates a force on the inlet tube assembly 14 that exceeds the spring constant k.

As alluded to above, one or more sealing bodies can be provided with the flow control device 10 for establishing a fluid seal at the chambers 18, 20. For example, in one embodiment a lower membrane 66 and an upper membrane 76 can be included. The lower membrane 66 and the upper membrane 76 are flexible membranes placed in ring-like configurations. The upper and lower membranes 66, 76 are expandable and/or contractable. In one embodiment, the upper and lower membranes 66, 76 are configured with a width that allows the upper and lower membranes 66, 76 to overlap upon themselves circumferentially. The upper and lower membranes 66, 76 are formed in a diameter appropriate to seal the inlet tube assembly 14 against the interior surface 28 of the housing assembly 12. The inner and outer perimeters of the upper and lower membranes 66, 76 may have applied adhesives, stops, clips or other means of attaching the upper and lower membranes 66, 76 within the housing assembly 12.

The flow regulating device 10 forms the constant pressure chamber 18 and the middle chamber 20 within the housing assembly 12. The middle chamber 20 is formed inside the main housing 22 between the valve seat body 24 of the housing assembly 12 and the flange 56 of the inlet tube assembly 14. The middle chamber 20 is open to ambient at the at least one bleed hole 32. As a point of reference, FIGS. 1 and 2 illustrate that the middle chamber 20 is sealed within the interior surface 28 of the main housing 22 between the upper and lower membranes 66, 76. In one embodiment, the lower membrane 66 connects to the interior surface 28 of the main housing 22 as well as the ridge 64 on the proximal region 62 of the tube 54. In another embodiment, the lower membrane 66 is attached to the flow port 46 instead of the main housing 22. This may occur when the flow port 46 and the main housing 22 are fabricated separately and later assembled. This provides for a lower fluid seal of the middle chamber 20.

Further, the middle chamber 20 is fluidly sealed from the constant pressure chamber 18 at the upper membrane 76. The flange 56 of the inlet tube assembly 14 is further sealed to the interior surface 28 of the housing 12 by the upper membrane 76. The upper membrane 76 is attached at the groove 36 of the main housing 22 and the groove 72 of the flange 56. The upper membrane 76 may be further secured to the housing assembly 12 by the hub 43 of the distal plate 26. Additionally, the upper membrane 76 may be further secured to the flange 56 by an O-ring 78.

The constant pressure chamber 18 is further formed by the distal plate 26 and the flange 56 of the inlet tube assembly 14, opposite the middle chamber 20. The distal plate 26 is sealably, and removably, connected to the main housing 22 at the circumferential recess 38. The constant pressure chamber 18 is positioned between the flange 56 of the inlet tube assembly 14 and the distal plate 26. The at least one extension 40 projects into the constant pressure chamber 18 and prevents complete closure between the distal plate 26 and the distal face 70 of the flange 56. As discussed previously, the upper membrane 76 provides a sealed body between the constant pressure chamber 18 and the middle chamber 20 formed within the housing assembly 12.

As assembled, the housing assembly 12 is configured to enclose the working components of the flow regulating device 10. In particular, the inlet tube assembly 14 is positioned within the housing assembly 12. The inlet tube assembly 14 is oriented within the housing assembly 12 such that the proximal end 50 is adjacent to the valve seat body 24 and the flange 56 is adjacent to the distal plate 26. As oriented, the radial wall 68 of the flange 56 extends beyond the channel 34 along the interior surface 28 of the main housing 22 and slidably moves along the interior surface 28 as the inlet tube assembly 14 is repositioned. Attached to the flange 56 along the outer rim 72 and the groove 36 of the main housing 22, the upper membrane 76 expands and/or contracts within the channel 34 as needed to accommodate the position of the inlet tube assembly 14. The upper membrane 76 is fluidly sealed to both the flange 56 and the housing assembly 12. The lower membrane 66 also provides a fluid seal and expands and/or contracts in response to the movement of the inlet tube assembly 14.

Additionally, the biasing mechanism 16 is enclosed within the middle chamber 20 of the flow regulating device 10. Respective ends of the biasing mechanism 16 may abut the proximal face 71 of the flange 56 and the valve seat body 24. In one embodiment, the radial wall 68 and the interior guide 52 maintain the position of the respective ends of the biasing mechanism 16 within the housing assembly 12. In another embodiment, the inner rim wall 74 positions the biasing mechanism 16 against the flange 56. The biasing mechanism 16 may also encircle the tube 54.

The flow regulating device 10 described above functions in the following manner. In general terms, the inlet tube assembly 14 slides between a first, open position (FIG. 1) in which airflow to the constant pressure chamber 18 is permitted and a second, closed position in which airflow to the constant pressure chamber 18 is prevented in establishing a near constant pressure flow of air from the outlet orifice 42. In the context of medical testing procedures, a patient's breath enters the gas flow regulating device 10 at the flow port 46 by means of an artificial airway (not shown) or directly from a patient's mouth, and is directed toward the proximal end 50 of the lumen 58 via the through holes 44 (FIG. 3) in the valve seat body 24. An uneven flow of the patient's breath is regulated to a constant flow that exits the gas flow regulating device 10 at the outlet orifice 42, allowing samples to be collected for analysis and testing (for example via a test tube (not shown) assembled to the distal plate 26 at the outlet orifice 42). More specifically and as illustrated by the flow arrows 80 in FIG. 2, the patient's exhaled breath enters the flow regulating device 10 by way of the through holes 44 and into the lumen 58 at the proximal end 50. The breath exits the lumen 58 at the distal end 60 of the inlet tube assembly 14 and is directed into the constant pressure chamber 18. The inlet tube assembly 14 slidably repositions within the housing assembly 12 as the volume of air (and thus pressure) increases in the constant pressure chamber 18.

In the one embodiment, a diameter of the outlet orifice 42 is smaller than a diameter of the lumen 58 of the inlet tube assembly 14. In this manner, only a portion of the delivered air exits the constant pressure chamber 18 via the outlet orifice 42. Pressure builds within the constant pressure chamber 18 as the volume of air in the constant pressure chamber 18 increases at a rate greater than the rate the contained air can exit through the outlet orifice 42. Pressure within the constant pressure chamber 18 builds until the force against the flange 56 of the slidable inlet tube assembly 14 is greater than the constant k of the biasing mechanism 16, forcing the inlet tube assembly 14 to slide proximally toward the valve seat body 24. The bleed hole 32 relieves any build-up of pressure within the middle chamber 20 in response to movement of the inlet tube assembly 14. When the proximal end 50 of the lumen 58 seals against the seat 48, airflow into the inlet tube assembly 14 (and thus to the constant pressure chamber 18) is prevented.

Conversely, as air is continuously released from the constant pressure chamber 18, the corresponding pressure (and thus force on the flange 56) will decrease; once the force drops below the spring constant k, the biasing device 16 forces the inlet tube assembly 14 back toward the open state. As a result, the flow rate of airflow exiting the outlet orifice 42 is constant, and is independent of any fluctuations from the patient. In this manner, a more constant volume of air passing through the flow regulating device 10 per unit time is achieved. Thereby, the flow of air through the critical orifice 42 is controlled at a constant rate, despite variations in the air pressure entering the flow control device 10 at the through holes 44.

Figure 5:
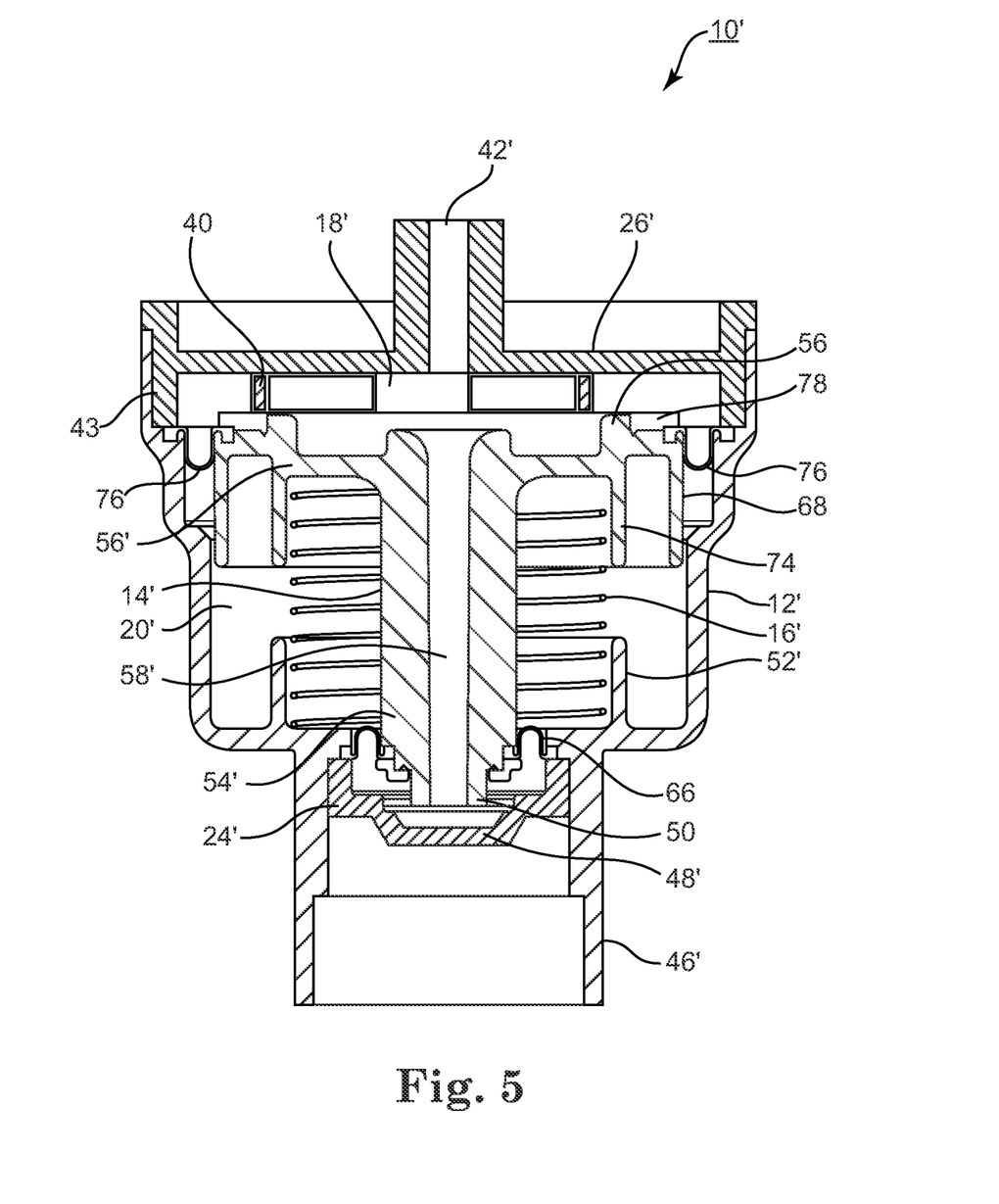
FIG. 5 is a sectional view of another flow regulating device in accordance with principles of the present disclosure in an open state.
Figure 6:
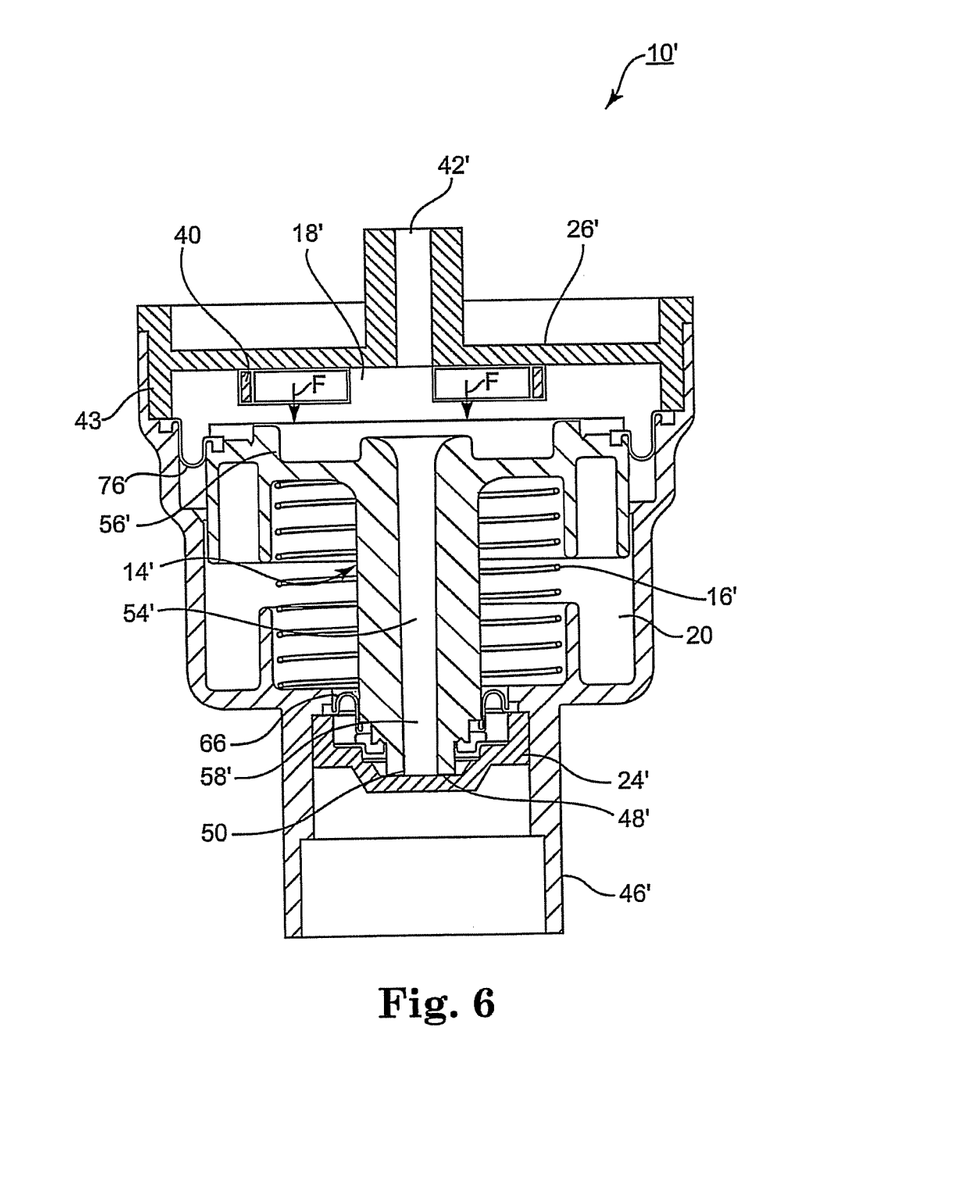
FIG. 6 is a sectional view of the flow regulating device of FIG. 5 in a closed state.

An alternate embodiment device 10' is provided in FIGS. 5 and 6 that further illustrate optional aspects of the present disclosure. The device 10' is highly akin to the device 10 (FIG. 1), and includes a housing assembly 12' slidably maintaining an inlet tube assembly 14' relative to a constant pressure chamber 18' and a middle chamber 20' between an open or first state (FIG. 5) and a closed or second state (FIG. 6).

In the first, open state, the inlet tube assembly 14' permits communication of a lumen 58' with the constant pressure chamber 18'. A flange 56' of the inlet tube assembly 14' is biased toward the open state by a biasing mechanism 16'. As compared to the flange 56 (FIG. 1) previously described, the flange 56' may have an inner rim wall 74 positioned radially within the radial wall 68' that provides guidance and/or stability to the biasing mechanism 16' as it interfaces with the flange 56'. Air exits through the distal plate 26' via the outlet orifice 42' defined by an outlet port 45 that otherwise extends from a major face of the distal plate 26' to provide convenient connection to a tube or medical device (not shown).

In the closed position of FIG. 6, pressure within the constant pressure chamber 18' generates a force F onto the flange 56' greater than a spring constant k of the biasing mechanism 16'. The biasing mechanism 16' is thus compressed by the flange 56' of the inlet tube assembly 14', and the inlet tube assembly 14' slides proximally to a sealed location with the seat 98' of the valve seat body 24'. Thus, the lumen 58' is sealed from the through holes (not shown, but akin to the through holes 44 of FIG. 3) such that the patient's breath cannot enter the constant pressure chamber 18' from the lumen 58'.

Although specific embodiments have been illustrated and described herein, it will be appreciated by those of ordinary skill in the art that a variety of alternate and/or equivalent implementations may be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. A gas flow regulating device for use as part of a medical system for sampling a patient's breath, the device comprising:
    a housing assembly including a main housing, a valve seat body, and a distal plate, the main housing forming an inlet port at a proximal end and the distal plate forming an outlet orifice; wherein adjacent to the inlet port at the proximal end, the valve seat body forms through holes
    an inlet tube assembly including a proximal inlet end, a tube forming a lumen, and a flange, the inlet tube assembly slidably disposed within the housing assembly;
    a lower membrane sealably connected between the inlet tube assembly proximal to the proximal inlet end and an interior surface of the housing, wherein a width of the lower membrane allows the lower membrane to overlap upon itself circumferentially;
    a biasing device disposed within the main housing and bearing against the flange of the inlet tube assembly;
    a middle chamber formed within the housing assembly between the proximal inlet end and the flange of the inlet tube assembly; and
    a constant pressure chamber formed within the housing assembly between the flange of the inlet tube assembly and the distal plate;
    wherein the valve seat body has an exterior circumferential surface and an interior circumferential surface, the interior circumferential surface comprising a tapering diameter to fluidly seal the proximal inlet end of the inlet tube;
    wherein the device is configured to provide an open state in which incoming airflow to the inlet port is directed to the constant pressure chamber via the lumen, and a closed state in which the lumen is fluidly sealed between the inlet port and the constant pressure chamber such that a constant airflow rate from the outlet orifice is provided independent of fluctuations in the incoming airflow rate at the inlet port.

2. The device of claim 1, further comprising an upper membrane sealably connected between the flange of the inlet tube assembly and an interior surface of the housing, fluidly separating the middle chamber from the constant pressure chamber.

3. The device of claim 1, wherein the biasing device is a spring.

4. The device of claim 1, wherein the biasing device is positioned in the middle chamber.

5. The device of claim 1, wherein the valve seat body includes an inlet tube seat.

6. The device of claim 1, wherein the housing forms a bleed hole at the middle chamber which is open to ambient.

7. The device of claim 1, wherein the distal plate includes at least one extension protruding into the constant pressure chamber.

8. The device of claim 1, wherein the flange of the inlet tube assembly includes a rim disposed against an interior surface of the housing assembly.

9. A method of regulating airflow, comprising:
   providing a flow regulating device comprising a housing assembly having an inlet port at a proximal end, a moveable inlet tube assembly, a membrane sealably connected between the inlet tube assembly and an interior surface of the housing assembly, and a biasing mechanism, the flow regulating device forming a first chamber and a second chamber;
   biasing the inlet tube assembly to an open state via the biasing mechanism;
   receiving incoming airflow from a patient at through openings formed in the housing assembly;
   directing the airflow from the through openings through a lumen in the inlet tube assembly and into the second chamber with the inlet tube assembly in the open state;
   restricting the airflow exiting the second chamber through an outlet orifice of the housing assembly; and
   transitioning the inlet tube assembly to a closed state in which the lumen is sealed relative to the second chamber by:
      increasing the airflow volume and pressure in the second chamber,
      compressing the biasing mechanism within the first chamber in response to the increased pressure in the second chamber,
      sliding the inlet tube assembly toward a valve seat with compression of the biasing mechanism, wherein a valve seat body has an exterior circumferential surface and an interior circumferential surface, the interior circumferential surface comprising a tapering diameter to fluidly seal the proximal inlet end of the inlet tube, wherein adjacent to the inlet port at the proximal end, the valve seat body forms through holes;
   wherein the membrane performs one of expanding and contracting in response to movement of the inlet tube assembly relative to the housing assembly.

10. The method of claim 9, further comprising maintaining a constant airflow rate exiting the flow regulating device.

11. The method of claim 9, further comprising the pressure generated by the airflow within the second chamber being exerted on a flange of the movable inlet tube assembly, the pressure exerted being greater than a resting force of the biasing mechanism.

12. The method of claim 11, further comprising the biasing mechanism maintaining a closed passageway of the inlet tube assembly against the valve seat until the pressure in the second chamber is less than the resting force of the biasing mechanism.

13. An exhalation valve assembly, comprising:
   a housing having a distal end and a proximal end, the housing forming an inlet port at the proximal end;
   a distal plate forming an orifice sealably connected to the housing;
   an inlet tube assembly slidably disposed within the housing having a proximal end a distal end, and a lumen extending between the proximal end and the distal end;
   a first chamber formed in the housing between the proximal end and the distal end of an inlet tube assembly;
   a second chamber formed in the housing between, and bounded by, the distal end of the inlet tube assembly and the distal plate, the second chamber being in fluid communication with the inlet tube assembly lumen;
   an upper flexible seal member connected to the housing and the distal end of the inlet tube assembly, the upper flexible seal member configured to expand and contract in response to movement of the inlet tube assembly;
   a lower flexible seal member connected to the housing and the proximal end of the inlet tube assembly, the lower flexible seal member configured to expand and contract in response to movement of the inlet tube assembly;
   a biasing mechanism contained within the first chamber and applying a biasing force to the inlet tube; and
   a valve seat body disposed at the proximal end of the housing, wherein the valve seat body has an exterior circumferential surface and an interior circumferential surface, the interior circumferential surface comprising a tapering diameter to fluidly seal the proximal inlet end of the inlet tube wherein adjacent to the inlet port at the proximal end, the valve seat body forms through holes.

14. The assembly of claim 13, wherein the housing forms at least one opening exposing the first chamber to ambient.

15. The assembly of claim 13, wherein the spring has a spring constant such that the spring will compress when airflow into the assembly is greater than the airflow expelled constant airflow from the assembly.

16. The assembly of claim 13, wherein the inlet tube assembly has a first position wherein a lumen within the inlet tube assembly is open at both the proximal end and the distal end of the tube.

17. The assembly of claim 16, wherein the inlet tube assembly has a second position wherein the lumen is closed against the proximal end of the housing.

18. The assembly of claim 16, wherein the first position is maintained by a predetermined force of the biasing mechanism.

* * * * *